United States Patent
Fujiwara et al.

(10) Patent No.: US 9,622,245 B2
(45) Date of Patent: Apr. 11, 2017

(54) RADIO COMMUNICATION DEVICE, CONTROL METHOD AND RADIO COMMUNICATION SYSTEM

(71) Applicant: Renesas Electronics Corporation, Tokyo (JP)

(72) Inventors: Taku Fujiwara, Tokyo (JP); Tomohiko Ohtsu, Tokyo (JP); Masamitsu Muratani, Tokyo (JP)

(73) Assignee: RENESAS ELECTRONICS CORPORATION, Tokyo (JP)

( * ) Notice: Subject to any disclaimer, the term of this patent is extended or adjusted under 35 U.S.C. 154(b) by 0 days.

(21) Appl. No.: 15/170,510

(22) Filed: Jun. 1, 2016

(65) Prior Publication Data

US 2017/0055258 A1 Feb. 23, 2017

(30) Foreign Application Priority Data

Aug. 21, 2015 (JP) ................. 2015-163407

(51) Int. Cl.

| H04B 7/00 | (2006.01) |
|---|---|
| H04M 3/00 | (2006.01) |
| H04M 1/00 | (2006.01) |
| H04W 72/04 | (2009.01) |
| H04W 72/12 | (2009.01) |
| H04W 74/00 | (2009.01) |

(Continued)

(52) U.S. Cl.
CPC ....... *H04W 72/0453* (2013.01); *H04W 4/008* (2013.01); *H04W 72/1215* (2013.01); *H04W 74/002* (2013.01); *H04W 88/06* (2013.01)

(58) Field of Classification Search
CPC ..... H04W 4/008; H04W 24/02; H04W 88/06; H04M 1/21
USPC ............ 455/41.1, 41.2, 41.3, 418, 419, 420, 455/552.1, 553.1
See application file for complete search history.

(56) References Cited

U.S. PATENT DOCUMENTS 7,873,384 B2* 1/2011 Karaoguz ........... H04L 41/0843
455/552.1
7,873,599 B2* 1/2011 Ishii .................... G06F 11/1451
707/640

(Continued)

FOREIGN PATENT DOCUMENTS

JP 2009-93370 A 4/2009

*Primary Examiner* — Quochien B Vuong
(74) *Attorney, Agent, or Firm* — McDermott Will & Emery LLP

(57) ABSTRACT

When a state of a radio communication device corresponds to a predetermined state, a communication control unit operates in the first mode to communicate according to the BLE standard, while when the radio communication device does not receive connect request packets, the communication control unit operates in the second mode to communicate. A rewrite switching unit switches to a rewritable state when the communication control unit operates in the first mode and to a rewriting prohibited state when the communication control unit operates in the second mode. The first mode is a mode for updating. In the first mode, the communication control unit transmits a notification for limiting the communication to the updating in an establishment process of the communication. The second mode is a mode for performing processing other than the updating. In the second mode, the communication control unit does not transmit the notification.

16 Claims, 13 Drawing Sheets

(51) Int. Cl.
*H04W 4/00* (2009.01)
*H04W 88/06* (2009.01)

(56) References Cited

U.S. PATENT DOCUMENTS

| | | | |
|---|---|---|---|
| 8,433,308 B2* | 4/2013 | Chen | H04W 48/12 |
| | | | 455/418 |
| 9,092,322 B2* | 7/2015 | Kanai | G06F 12/1425 |
| 9,396,346 B2* | 7/2016 | Willis | G06F 21/53 |

* cited by examiner

RADIO COMMUNICATION DEVICE, CONTROL METHOD AND RADIO COMMUNICATION SYSTEM

CROSS-REFERENCE TO RELATED APPLICATIONS

This application is based upon and claims the benefit of priority from Japanese patent application No. 2015-163407, filed on Aug. 21, 2015, the disclosure of which is incorporated herein in its entirety by reference.

BACKGROUND

The present application relates to a radio communication device, a control method, and a radio communication system and to, for example, a radio communication device, a control method, and a radio communication system that update software.

Recently, radio communication devices compliant with the BLE (Bluetooth Low Energy), which is a low-power standard for Bluetooth (registered trademark) have been developed. Such radio communication devices, for example, provide various services using communication according to BLE by software. It may be necessary to update the software mounted on the radio communication devices due to various reasons such as changes in software specifications. It is thus desired for each of the radio communication devices to include a configuration that updates the software in the corresponding radio communication device.

Japanese Unexamined Patent Application Publication No. 2009-93370 discloses a technique in which a ROM previously storing a plurality of types of device drivers is mounted, and a necessary device driver(s) is read from this ROM in order to change the device driver(s).

SUMMARY

It is desired to easily update software that is mounted on a radio communication device.

Other problems of the related art and new features of the present invention will become apparent from the following descriptions of the specification and attached drawings.

According to an aspect, a radio communication device includes a communication control unit that, when a state of a radio communication device corresponds to a predetermined state, operates in a first mode to communicate according to the BLE standard, while when the radio communication device does not receive connect request packets, the communication control unit operates in a second mode to communicate. The radio communication device further includes a rewrite switching unit that switches to a rewritable state when the communication control unit operates in the first mode and to a rewriting prohibited state when the communication control unit operates in the second mode. The first mode is a mode for updating. In the first mode, the communication control unit transmits a notification for limiting the communication to the updating in an establishment process of the communication. The second mode is a mode for performing processing other than the updating. In the second mode, the communication control unit does not transmit the notification for limiting the communication to the updating.

According to the above aspect, it is possible to easily update software mounted on a radio communication device.

BRIEF DESCRIPTION OF THE DRAWINGS

The above and other aspects, advantages and features will be more apparent from the following description of certain embodiments taken in conjunction with the accompanying drawings, in which.

DETAILED DESCRIPTION

Figure 1:
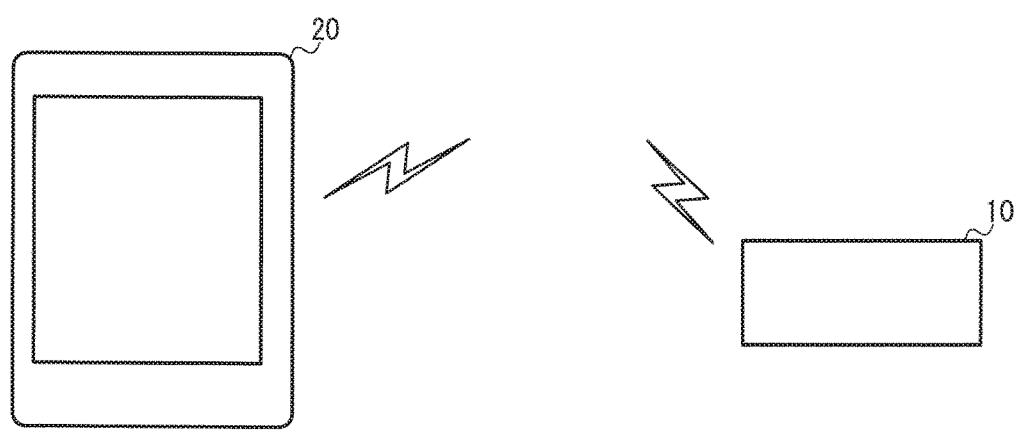
FIG. 1 is a schematic diagram showing a configuration of a radio communication system according to an embodiment.

The following descriptions and drawings are omitted and simplified as appropriate for clarity of the descriptions. Further, the elements illustrated in the drawings as functional blocks for performing various processes can be implemented hardware-wise by a CPU, a memory, and other circuits, and software-wise by a program loaded onto a memory or the like. Accordingly, it is to be understood by those skilled in the art that these functional blocks can be implemented in various forms including, but not limited to, being implemented by hardware alone, software alone, or a combination of hardware and software. Note that in the drawings, the same elements are denoted by the same reference signs, and repeated descriptions will be omitted as needed.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Description of Radio Communication Device According to Comparative Example

A comparative example examined by the inventor will be described prior to giving descriptions of embodiments. To prevent malfunctions and for security reasons, it is necessary to prohibit free rewriting in a storage unit that stores software used to operate a radio communication device. Thus, the radio communication device needs to have a configuration that can switch between a rewritable state in which rewriting of the software in the storage unit is granted and a rewriting prohibited state in which rewriting of the software is prohibited. The radio communication device according to the comparative example includes a switch for updating software. The radio communication device according to the comparative example is configured in such a way that when a user operates the switch, a state of the radio communication device is switched to the rewritable state.

Figure 15:
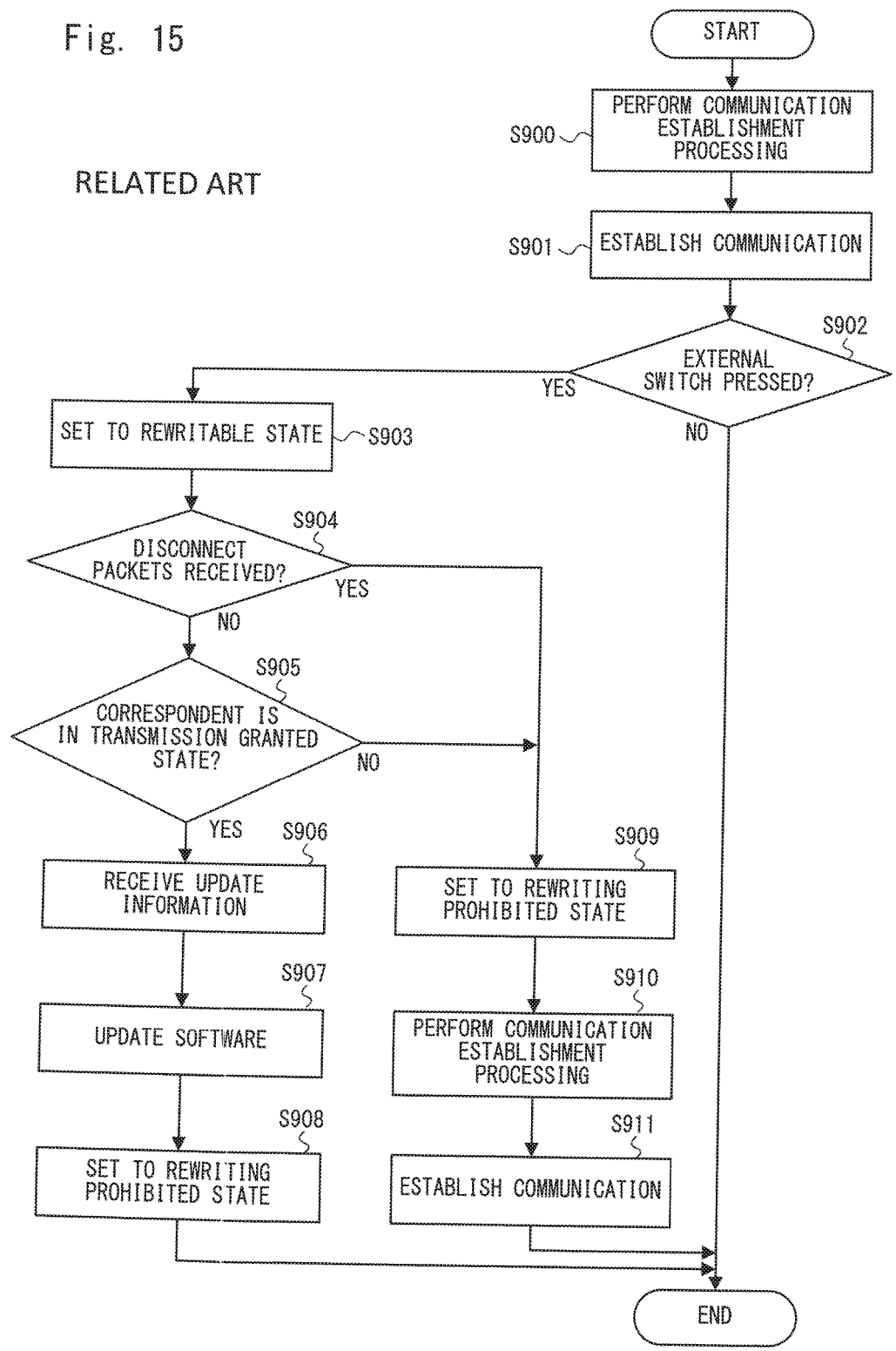
FIG. 15 is a flowchart showing an example of an operation of a radio communication device according to a comparative example.

To be more specific, the radio communication device according to the comparative example operates as shown in FIG. 15. FIG. 15 is a flowchart showing an example of an operation of the radio communication device according to the comparative example. A flow of the operation of the radio communication device according to the comparative example will be described by referring to FIG. 15.

In the step 900 (S900), the radio communication device according to the comparative example performs processing to establish radio communication by the BLE with a transmission device that transmits update information for updating the software. The radio communication device according to the comparative example performs, for example, processing shown in FIG. 5, which will be described later, as the processing to establish communication. Then, in the step 901 (S901) the radio communication device according to the comparative example establishes communication with the transmission device that transmits the update information. Note that as the communication established in the step 901 is, for example, in accordance with profiles that specify the communication when the radio communication device functions as a heart rate meter, updating of software is not planned in the communication established in the step 901. At this time, the radio communication device according to the comparative example is set to the rewriting prohibited state.

Therefore, when the user wants to update the software, the user needs to press the switch included in the radio communication device according to the comparative example. In the step 902, it is evaluated as to whether or not the switch is pressed. When the switch is pressed, the process moves to the step 903, while when the switch is not pressed, a series of processes will be ended.

In the step 903, the radio communication device according to the comparative example is set to the rewritable state. That is, the state is switched from the rewriting prohibited state to the rewritable state. After that, in the step 904, the radio communication device according to the comparative example evaluates as to whether or not Disconnect packets, which request a disconnection of the communication, have been received. When the Disconnect packets have been received, the process moves to the step 909. When the Disconnect packets have not been received, in the step 905 (S905), it is evaluated as to whether or not a correspondent is in a transmission granted state. The transmission granted state indicates a state in which transmission of the update information is granted. When the correspondent is not in the transmission granted state, the process moves to the step 909. When the correspondent is in the transmission granted state, in the step 906 (S906), the radio communication device according to the comparative example receives the update information. Next, in the step 907 (S907), the radio communication device according to the comparative example updates the software, and then in the step 908 (S908), the radio communication device according to the comparative example is set to the rewriting prohibited state again.

On the other hand, also when the process moves to the step 909 (S909), the radio communication device according to the comparative example is set to the rewriting prohibited state. After that, the radio communication device according to the comparative example performs an establishment processing of communication again. More specifically, in a manner similar to the steps 900 and 901, a communication establishment process (step 910) and establishment of communication (step 911) are performed.

In such a radio communication device according to the comparative example, the switch for updating the software needs to be included therein as described above. This increases the cost of the radio communication device and requires time and effort by the user.

Note that, for example, as a configuration of the radio communication device, a ROM may be included therein that previously stores another piece of software different from software currently used, so that the software currently used can be switched to the other piece of software. However, in this configuration, there is the following problem. Firstly, in such a configuration, the software currently used can be changed only to the software already stored in the ROM. Further, the ROM needs to be previously included in the radio communication device, thereby increasing the cost.

First Embodiment

Description of Radio Communication System 1

A first embodiment will be described in detail with reference to the drawings. FIG. 1 is a schematic diagram showing a configuration of a radio communication system 1 according to the first embodiment. The radio communication system 1 includes a radio communication device 10 and a radio communication device 20. The radio communication devices 10 and 20 perform radio communication. More specifically, the radio communication devices 10 and 20 perform radio communication compliant with the Bluetooth (registered trademark) Low Energy (BLE) standard. In this embodiment, updating of software in the radio communication device 10 by so-called OTA (Over The Air) in the radio communication system 1 will be described. The radio communication system 1 executes processing using communication according to BLE. In this embodiment, as an example of such processing, the radio communication system 1 performs processing related to measurement of a heart rate of a user. That is, the radio communication system 1 operates as a heart rate meter system. The radio communication device 10 is, for example, a wearable terminal provided with the functions of a heart rate meter. The radio communication device 20 is, for example, a portable terminal such as a smartphone, a tablet terminal, or the like that receives heart rate information measured by the radio communication device 10 through communication according to BLE and performs various information processes such as displaying the heart rate information. Note that in the communication according to BLE, the radio communication device 10 functions as a slave device (an advertiser), and the radio communication device 20 functions as a master device (an initiator).

(Description of Radio Communication Device 10)

Figure 2:
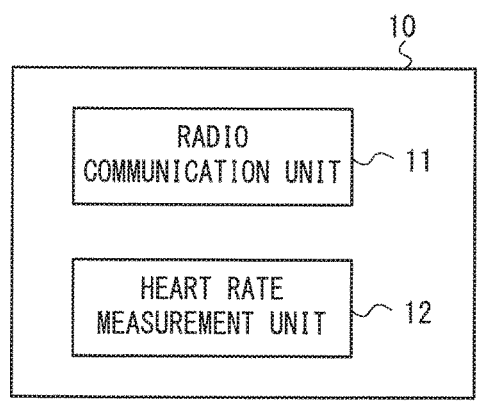
FIG. 2 is a block diagram showing an example of a configuration of a first radio communication device according to the embodiment.

FIG. 2 is a block diagram showing an example of the configuration of the radio communication device 10. The radio communication device 10 includes a radio communication unit 11 and a heart rate measurement unit 12. The heart rate measurement unit 12 includes a heart rate sensor comprised of a light emitter, a light receiver, and the like and measures a heart rate of the user. The radio communication device 10 wirelessly communicates by the radio communication unit 11, which will be described later, in regard to various information items including the heart rate information measured by the heart rate measurement unit 12.

Figure 3:
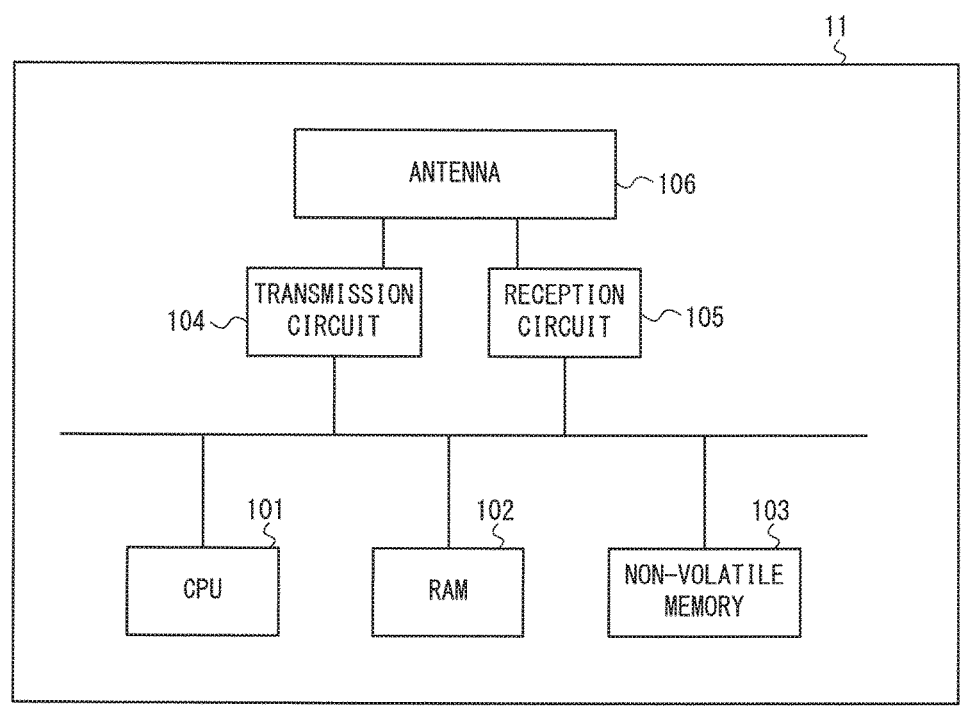
FIG. 3 is a block diagram showing an example of a hardware configuration of a radio communication unit of the first radio communication device according to the embodiment.

FIG. 3 is a block diagram showing a hardware configuration of the radio communication unit 11 of the radio communication device 10. The radio communication unit 11 includes, as shown in FIG. 3, a CPU (Central Processing Unit) 101, a RAM (Random Access Memory) 102, a non-volatile memory 103, a transmission circuit 104, a reception circuit 105, and an antenna 106.

The non-volatile memory 103 stores software such as firmware. The non-volatile memory 103 stores, for example, software that executes communication processing according to BLE. In this embodiment, to be more specific, the non-volatile memory 103 stores BLE profiles. In this embodiment, the profiles stored in the non-volatile memory 103 include profiles that specify communication as a heart rate meter system (e.g., Heart Rate Profiles). Note that the non-volatile memory 103 may be referred to as a storage unit.

The transmission circuit 104 transmits data via the antenna 106 under control by a communication control unit 153, which will be described later. The transmission circuit 104, for example, modulates and amplifies the transmission data and emits it as radio waves from the antenna 106. Likewise, the reception circuit 105 receives data via the antenna 106 under control by the communication control unit 153, which will be described later. The reception circuit 105, for example, amplifies and demodulates radio waves received by the antenna 106 and captures them as reception data. Note that the transmission circuit may be referred to as a transmission unit. Moreover, the reception circuit may be referred to as a reception unit.

Figure 4:
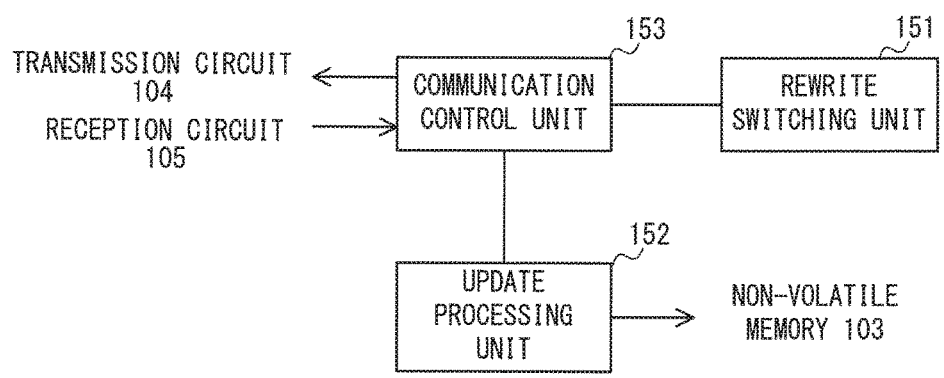
FIG. 4 is a block diagram showing an example of a functional configuration of the radio communication unit of the first radio communication device according to the embodiment.

FIG. 4 is a block diagram showing an example of a functional configuration of the radio communication unit 11 of the radio communication device 10. As shown in FIG. 4, the radio communication unit 11 includes a rewrite switching unit 151, an update processing unit 152, and a communication control unit 153. The rewrite switching unit 151, the update processing unit 152, and the communication control unit 153 can be achieved, for example, by executing programs under control by the CPU 101. This program is stored in, for example, the non-volatile memory 103.

The rewrite switching unit 151 switches between whether to grant rewriting of the software in the non-volatile memory 103 or not. As described above, it is necessary to prohibit free rewriting in the non-volatile memory 103. Therefore, the rewrite switching unit 151 switches between a rewritable state in which the software in the non-volatile memory 103 can be rewritten and a rewriting prohibited state in which the rewriting of the software in the non-volatile memory 103 is prohibited. This prevents immoderate rewriting of program storage regions.

The rewrite switching unit 151 switches to the rewritable state when the communication control unit 153 operates in an updating mode, which will be described later, and to the rewriting prohibited state when the communication control unit 153 operates in a normal mode, which will be described later.

The update processing unit 152 performs processing to update the software. The update processing unit 152 updates the software stored in the non-volatile memory 103. Note that the update processing unit 152 may perform processing to add new software to the non-volatile memory 103 in the update processing. When the communication between the radio communication devices 10 and 20 is established in the updating mode, which will be described later, the update processing unit 152 executes the updating. To be more specific, update information received by the reception circuit 105 from the radio communication device 20 in the communication according to BLE is applied to the software to be updated that is stored in the non-volatile memory 103. Then, the update processing unit 152 updates the software to be updated that is stored in the non-volatile memory 103. Thus, the update processing unit 152 can apply the update information received from the radio communication device 20 and update the profiles that specify communication as a heart rate meter system.

The communication control unit 153 performs control so that communication compliant with the BLE standard is performed using the transmission circuit 104 and the reception circuit 105.

(Description of Establishment of Communication in Accordance with BLE Standard)

Figure 5:
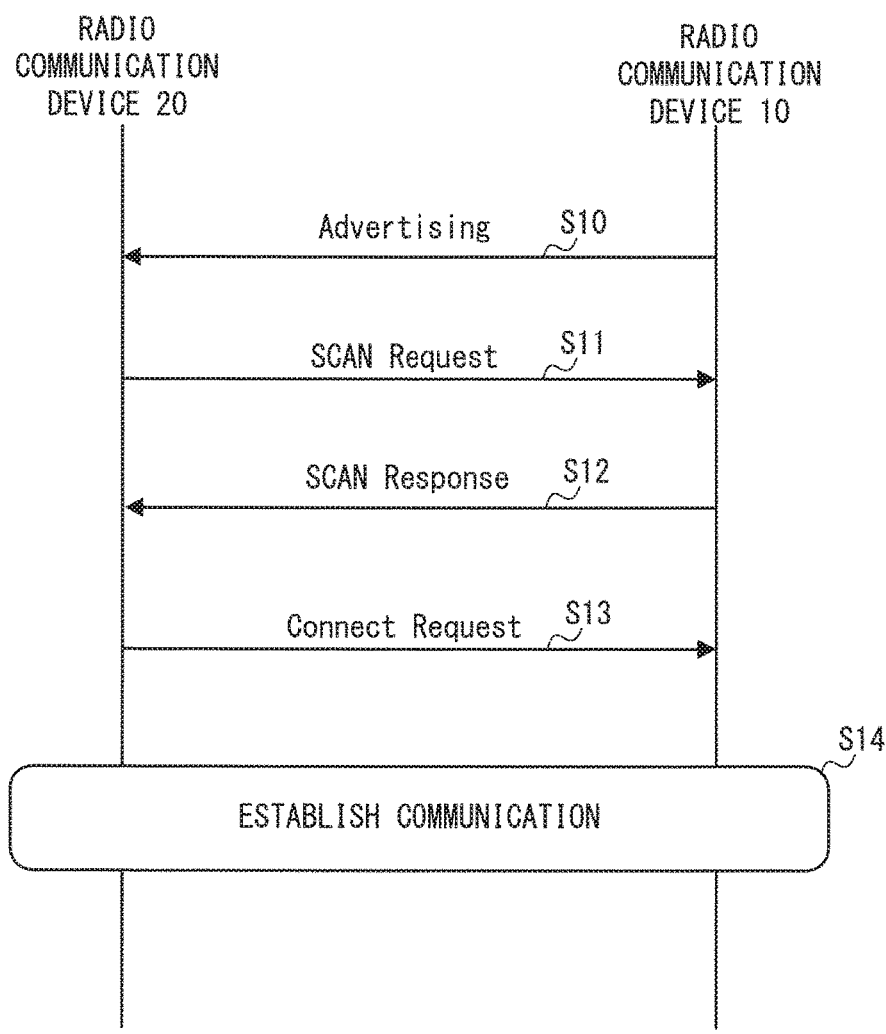
FIG. 5 is a sequence chart showing an establishment process of communication according to the BLE standard.

A flow of processing to establish communication according to the BLE standard will be described below. FIG. 5 is a sequence chart showing a process of establishing the communication according to the BLE standard. As shown in FIG. 5, in the communication according to the BLE standard, operations in the steps 10 to 13 are performed between the radio communication devices 10 and 20 until the communication is established. Hereinafter, operations for establishing the communication will be described by referring to FIG. 5.

In the step 10 (S10), the radio communication device 10, which is the slave device (the advertiser) transmits Advertising packets. The Advertising packets are for enabling the advertiser to find a correspondent to which the advertiser will be wirelessly connected and include information indicating a device name, functions, and the like of the advertiser. The transmitted Advertising packets are received by the radio communication device 20, which is the master device (the initiator).

In the step 11 (S11), the radio communication device 20 transmits SCAN Request packets to the radio communication device 10 that has transmitted the Advertising packets. The SCAN Request packets are for enabling the initiator that has received the Advertising packets to send a request for more information to the radio communication device 10 that has transmitted the Advertising packets.

In the step 12 (S12), the radio communication device 10 transmits SCAN Response packets to the radio communication device 20, which has transmitted the SCAN Request Packets. The SCAN Response packets can include information not transmitted in the Advertising packets.

In the step 13 (S13), the radio communication device 20 evaluates as to whether or not the radio communication device 10 has any problem as the correspondent according to the information obtained from the radio communication device 10, and if it does, transmits Connect Request packets to the radio communication device 10. The Connect Request packets request establishment of communication.

In the step 14 (S14), when the radio communication device 10 receives the Connect Request packets from the radio communication device 20, the communication according to BLE is established between the radio communication devices 10 and 20. Note that after the communication is established, the radio communication devices 10 and 20 may transmit Disconnect packets to the correspondents in order to disconnect the communication.

(Description of Radio Communication Device 10 (Communication Control Unit 153) Continued)

The communication control unit 153 performs control to operate as shown in FIG. 5 in order to establish the communication. The communication control unit 153 performs control to communicate according to the BLE standard in the updating mode or the normal mode.

The updating mode is also referred to as a first mode and is a mode in which the update information for updating the software stored in the non-volatile memory 103 is received from the radio communication device 20 in order to update the software. In the updating mode, the communication control unit 153 performs control to transmit a notification for limiting the communication to the updating to another device in the establishment process of the communication. To be more specific, the communication control unit 153 performs control to transmit the SCAN Response packets including the notification indicating that a condition for establishing communication is to include the update information in response to the SCAN Request packets from the other device. In this way, the radio communication device 10, which is the slave device, presents the condition for establishing radio communication by a SCAN response in response to a SCAN request from the master device.

The normal mode is also referred to as a second mode and is a mode for performing processing other than the updating of the software. The normal mode is, for example, a mode for performing communication in accordance with the profiles that specify the communication as a heart rate meter system. In the normal mode, unlike the updating mode, the communication control unit 153 performs control so that the notification for limiting the communication to the updating will not be transmitted to the other device in the establishment process of communication. More specifically, the communication control unit 153 transmits the SCAN Response packets that do not notify the other device that the condition for establishing communication is to include the update information in response to the SCAN Request packets from the other device. That is, for example, the communication control unit 153 performs control to transmit, in response to the SCAN Request packets from the other device, the SCAN Response packets including the notification indicating that the condition for establishing communication is not to include the update information, the SCAN Response packets that request conditions for establishing communication other than the condition of whether or not the update information is included, or the SCAN Response packets that do not specify any condition for establishing communication.

When a state of the radio communication device 10 corresponds to a predetermined state, the communication control unit 153 operates in the updating mode, and when the Connect Request packets have not been received from the other device in the communication establishment process in the updating mode, the communication control unit 153 operates in the normal mode. To be more specific, in this embodiment, the predetermined state is a state when the radio communication device 10 is activated. Accordingly, in this embodiment, the communication control unit 153 operates in the updating mode when the radio communication device 10 is activated. Then, the communication control unit 153 establishes communication when the communication control unit 153 receives the Connect Request packets from the other device in the above communication establishment process in the updating mode. On the other hand, when the communication control unit 153 does not receive the Connect Request packets from the other device in the above communication establishment process in the updating mode, the communication control unit 153 operates in the normal mode and attempts to establish communication in the above communication establishment process in the normal mode.

(Description of Radio Communication Device 20)

Figure 6:
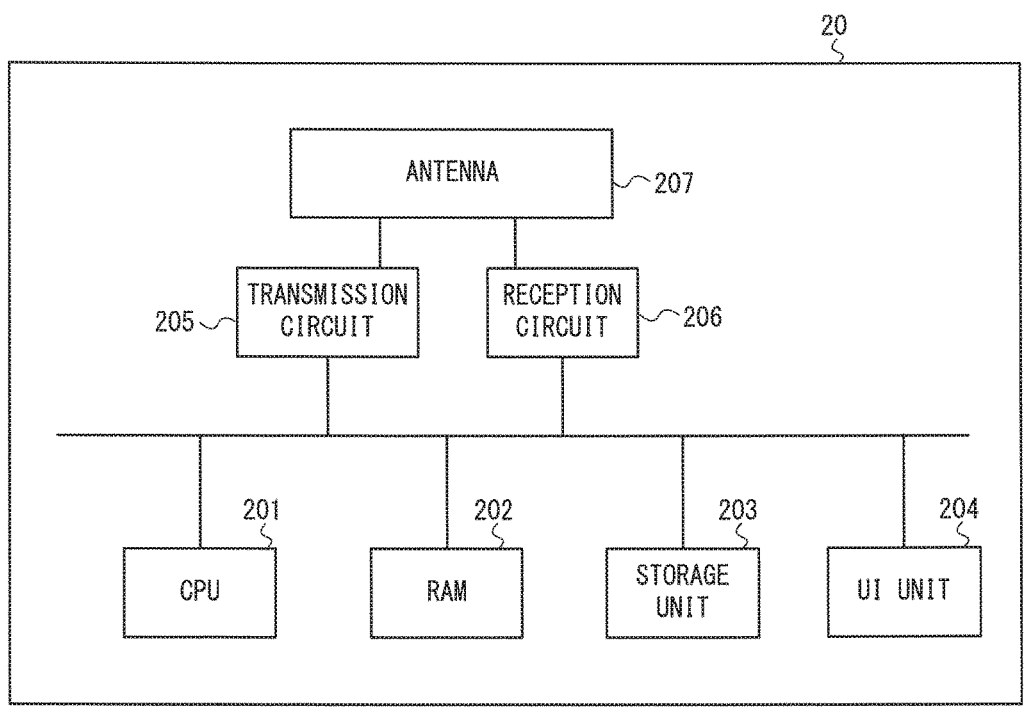
FIG. 6 is a block diagram showing an example of a hardware configuration of a second radio communication device according to the embodiment.

FIG. 6 is a block diagram showing an example of a hardware configuration of the radio communication device 20. The radio communication device 20 includes, as shown in FIG. 6, a CPU 201, a RAM 202, a storage unit 203, a UI (User Interface) unit 204, a transmission circuit 205, a reception circuit 206, and an antenna 207. The radio communication device 20 communicates as a heart rate meter system with the radio communication device 10 by the communication established in the normal mode of the radio communication device 10. Further, the radio communication device 20 transmits the update information for updating the software stored in the non-volatile memory 103 of the radio communication device 10 by the communication established in the updating mode of the radio communication device 10.

An application that provides functions of, for example, a heart rate meter system, is installed on the radio communication device 20 and performs various information processes such as displaying the heart rate information measured by the radio communication device 10.

When the radio communication device 20 obtains the update information, the obtained update information is stored in the storage unit 203. Note that the radio communication device 20 can obtain the update information by any method. For example, the radio communication device 20 may obtain the update information by downloading it via a network (not shown) such as the Internet or receive the update information by communication according to BLE from another radio communication device. Alternatively, the radio communication device 20 may obtain the update information by reading the update information stored in a portable storage medium such as a memory card.

The UI unit 204 includes, for example, a touch panel and accepts inputs of information and outputs information. The transmission circuit 205 transmits data under control by a communication control unit 251, which will be described later, via the antenna 207. The transmission circuit 205, for example, modulates and amplifies transmission data and emits the transmission data as radio waves from the antenna 207. Likewise, the reception circuit 206 receives the data under control by the communication control unit 251, which will be described later, via the antenna 207. The reception circuit 206, for example, amplifies and demodulates the radio waves received by the antenna 207 and captures the radio waves as reception data.

Figure 7:
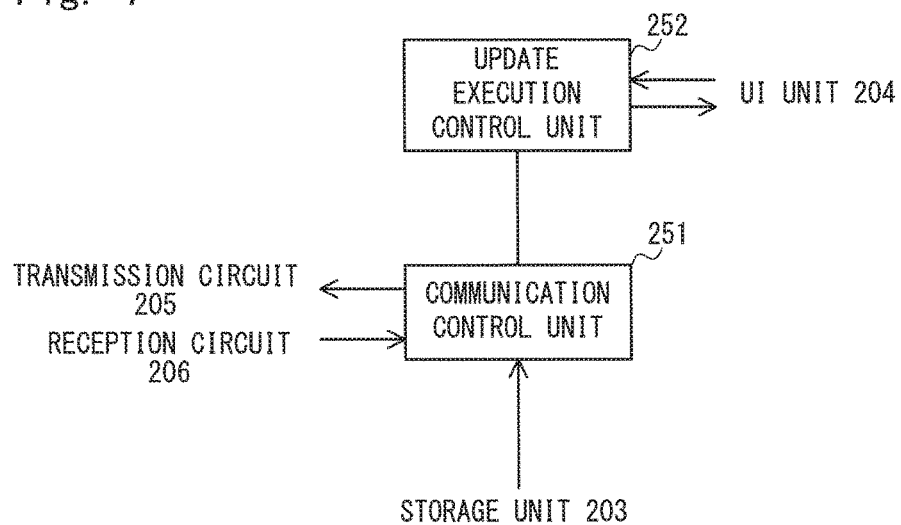
FIG. 7 is a block diagram showing an example of a functional configuration of the second radio communication device according to the embodiment.

FIG. 7 is a block diagram showing an example of a functional configuration of the radio communication device 20. As shown in FIG. 7, the radio communication device 20 includes a communication control unit 251 and an update execution control unit 252. The communication control unit 251 and the update execution control unit 252 can be achieved by, for example, executing a program by control of the CPU 201. The program is stored in, for example, the storage unit 203.

The communication control unit 251 uses the transmission circuit 205 and the reception circuit 206 to perform control to communicate according to the BLE standard. To be more specific, the communication control unit 251 establishes communication by performing control to execute the operations shown in FIG. 5. When the communication control unit 251 receives the notification from the radio communication device 10 indicating that the communication is limited to the updating in the establishment process of the communication, if the communication to be established has no problem in being used as the communication for the updating, the communication control unit 251 performs control to transmit the Connect Request packets to the radio communication device 10. More specifically, when the radio communication device 20 receives the SCAN Response packets including the notification indicating that the condition for establishing communication is to include the update information, the communication control unit 251 evaluates as to whether or not the storage unit 203 stores the update information, and when it does, the communication control unit 251 transmits the Connect Request packets in response to the SCAN Response packets.

In order to disconnect the communication, the communication control unit 251 transmits the Disconnect packets to the correspondent. Then, the communication is disconnected. For example, the communication control unit 251 may transmit the Disconnect packets according to an input instruction from the user via the UI unit 204.

When the communication is established according to the updating mode of the radio communication device 10, the communication control unit 251 evaluates as to whether or not a state of the radio communication device 20 is in a transmission granted state. When the state of the radio communication device 20 is in the transmission granted state, the communication control unit 251 performs control to read the update information stored in the storage unit 203 and transmits it via the transmission circuit 205. Note that the communication control unit 251 may transmit a notification to the radio communication device 10 indicating as to whether the state of the radio communication device 20 is in the transmission granted state or in a transmission prohibited state.

Figure 8:
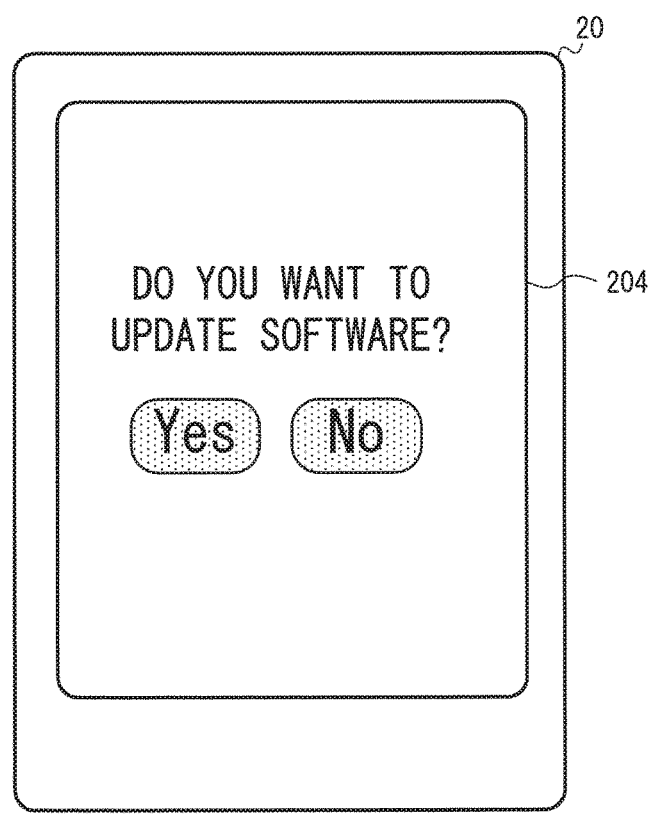
FIG. 8 is a drawing showing an example of a display that checks with a user as to whether or not to execute updating.

The update execution control unit 252 performs control on whether or not to transmit the update information. That is, the update execution control unit 252 sets the state of the radio communication device 20 to the transmission granted state or a state in which transmission of the update information is prohibited (the transmission prohibited state). When the communication is established according to the updating mode of the radio communication device 10, for example, as shown in FIG. 8, the update execution control unit 252 outputs a display to the UI unit 204 to check with the user as to whether or not the updating can be executed. When an instruction for granting the execution of the updating is input via the UI unit 204, the update execution control unit 252 sets the state of the radio communication device 20 to the transmission granted state. On the other hand, when an instruction indicating that the execution of the updating is not granted is input via the UI unit 204, the update execution control unit 252 sets the state of the radio communication device 20 to the transmission prohibited state. Thus, when the user does not want to execute the updating, the user can reject the updating.

(Description of Operation of Radio Communication Device 10)

Figure 9:
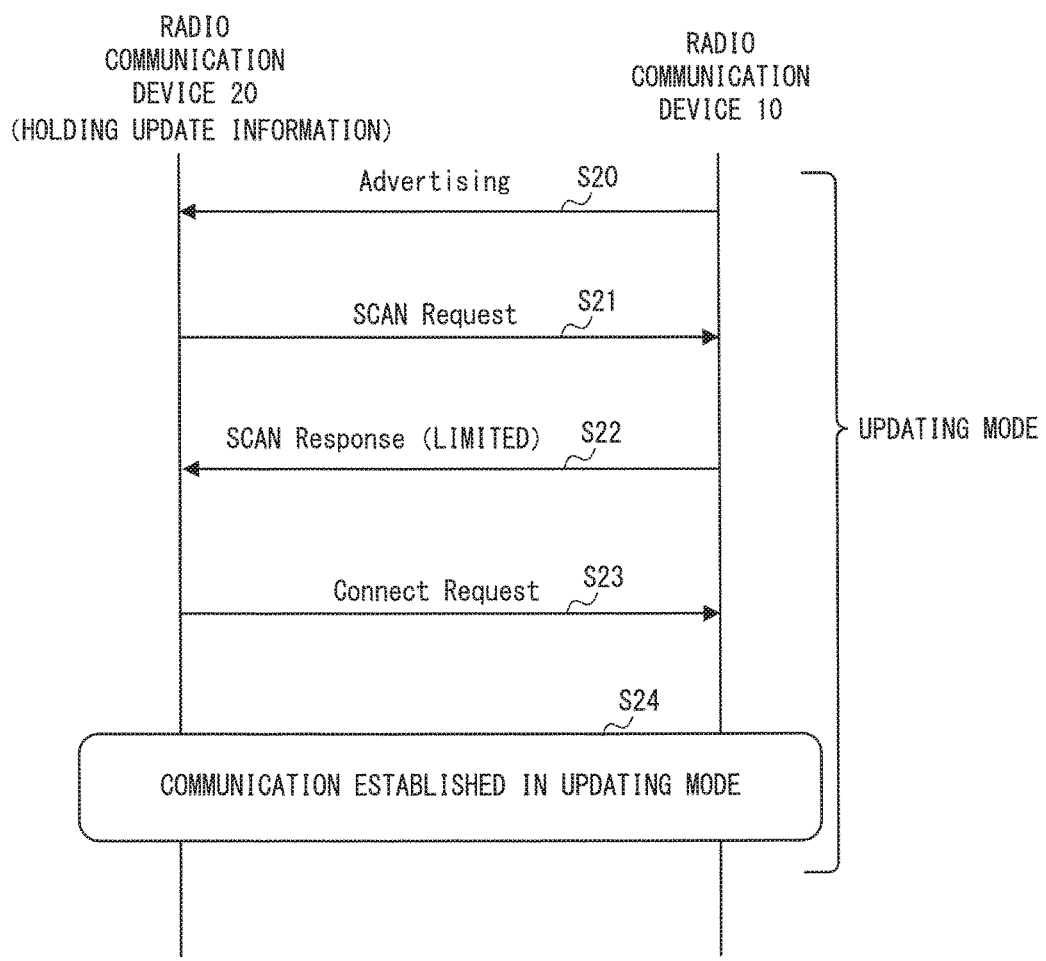
FIG. 9 is a sequence chart showing an example of an establishment process of communication when the second radio communication device holds update information.
Figure 10:
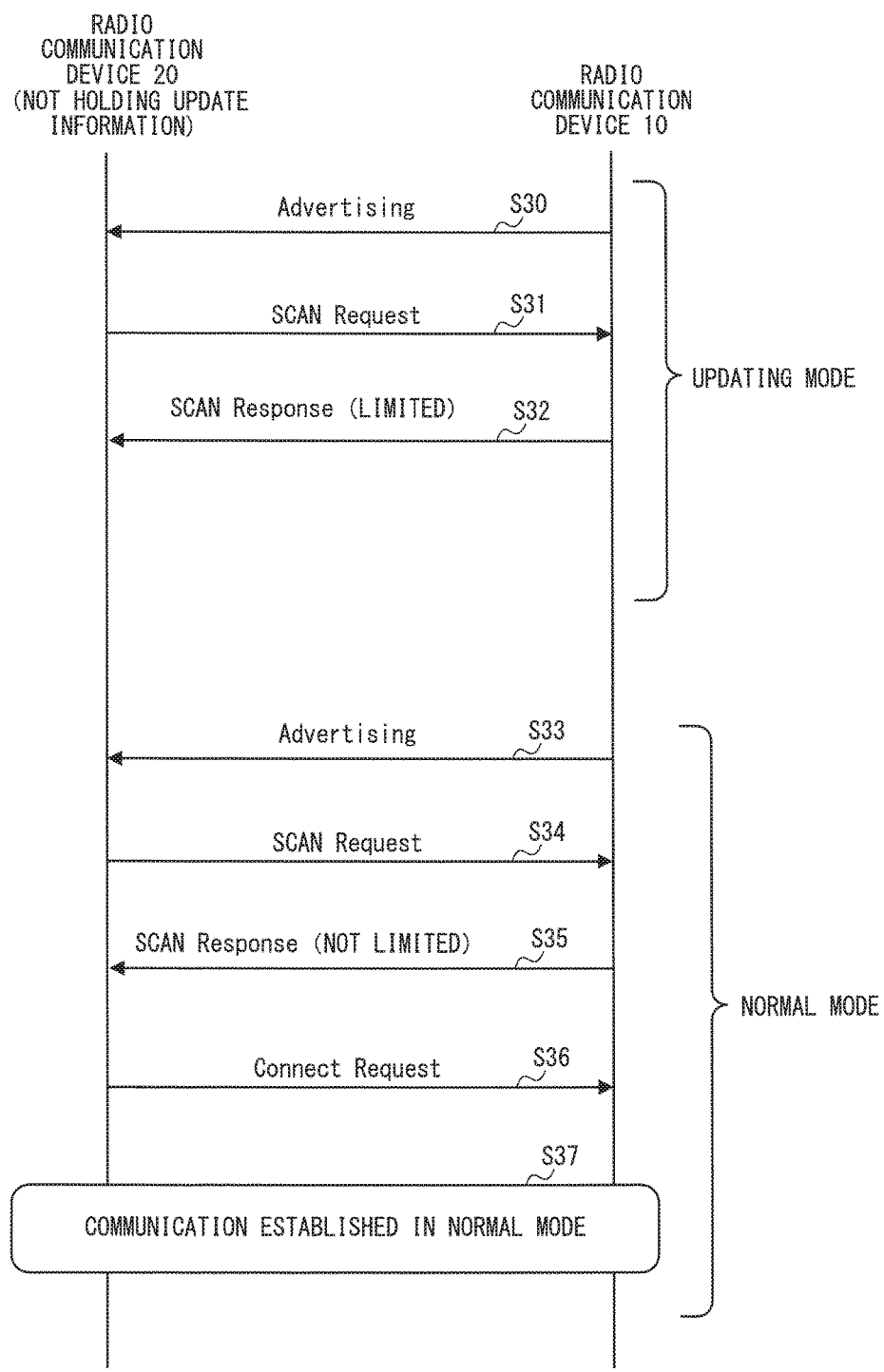
FIG. 10 is a sequence chart showing an example of an establishment process of communication when the second radio communication device does not hold the update information.

Next, an operation of the radio communication device 10 will be described. In this embodiment, as described above, the communication control unit 153 of the radio communication device 10 firstly attempts to establish the communication with the radio communication device 20 in the updating mode. When the establishment of the communication in the updating mode fails, the communication control unit 153 of the radio communication device 10 attempts to establish the communication in the normal mode. This operation will be further described by referring to FIGS. 9 and 10. FIG. 9 is a sequence chart showing an example of the establishment process of the communication when the radio communication device 20 holds the update information. On the other hand, FIG. 10 is a sequence chart showing an example of the establishment process of the communication when the radio communication device 20 does not hold the update information.

FIG. 9 will be described below. The radio communication device 10 operates in the updating mode after it is activated. Thus, the communication control unit 153 of the radio communication device 10 attempts to establish the communication in the updating mode. Firstly, in the step 20 (S20), the communication control unit 153 of the radio communication device 10 performs control to transmit the Advertising packets. Then, the Advertising packets are transmitted, and the radio communication device 20 receives the Advertising packets.

Next, in the step 21 (S21), the communication control unit 251 of the radio communication device 20 performs control to transmit the SCAN Request packets to the radio communication device 10. Then, the SCAN Request packets are transmitted, and the radio communication device 10 receives the SCAN Request packets.

Next, in the step 22 (S22), the communication control unit 153 of the radio communication device 10 performs control to transmit the SCAN Response packets including the notification for limiting a purpose of the communication to the communication for the updating. That is, the communication control unit 153 performs control to transmit the SCAN Response packets including the notification indicating that the condition for establishing communication is to include the update information. Then, the SCAN Response packets are transmitted, and the radio communication device 20 receives the SCAN Response packets.

Then, in the step 22, when the radio communication device 20 receives the SCAN Response packets, the communication control unit 251 of the radio communication device 20 evaluates as to whether or not the radio communication device 10 has any problem as a correspondent according to the information obtained from the SCAN Response packets. More specifically, the communication control unit 251 checks as to whether or not the storage unit 203 holds the update information. In the example shown in FIG. 9, as the update information is stored in the storage unit 203 of the radio communication device 20, the communication control unit 251 determines that the radio communication device 10 is considered appropriate as a correspondent. Thus, in the step 23 (S23), the communication control unit 251 of the radio communication device 20 performs control to transmit the Connect Request packets to the radio communication device 10. Then, the Connect Request packets are transmitted, and the radio communication device 10 receives the Connect Request packets.

Then, in the step 24 (S24), the communication in the updating mode is established between the radio communication devices 10 and 20.

Next, FIG. 10 will be described. In a manner similar to the example shown in FIG. 9, the radio communication device 10 operates in the updating mode after it is activated. Thus, the communication control unit 153 of the radio communication device 10 firstly attempts to establish communication in the updating mode. As the operations from the steps 30 (S30) to 32 (S32) are the same as the operations from the above steps 20 to 22, descriptions of the steps 30 (S30) to 32 (S32) will be omitted.

When the radio communication device 20 receives the SCAN Response packets in the step 32, the communication control unit 251 of the radio communication device 20 checks as to whether or not the storage unit 203 holds the update information. In the example shown in FIG. 10, as the update information is not stored in the storage unit 203 of the radio communication device 20, the communication control unit 251 determines that the radio communication device 10 is not appropriate as a correspondent. Thus, the communication control unit 251 of the radio communication device 20 performs control so that the Connect Request packets will not be transmitted to the radio communication device 10. Accordingly, the Connect Request packets are not transmitted from the radio communication device 20, and the radio communication device 10 cannot receive the Connect Request packets.

When the communication control unit 153 of the radio communication device 10 cannot receive the Connect Request packets within a predetermined time after the communication control unit 153 of the radio communication device 10 transmitted the Scan Response packets, the communication control unit 153 of the radio communication device 10 attempts to establish the communication in the normal mode. That is, when the radio communication device 10 fails to establish the communication in the updating mode, the radio communication device 10 operates in the normal mode. Thus, the rewrite switching unit 151 switches to the rewriting prohibited state.

Then, in the steps 33 (S33) and 34 (S34), in a manner similar to the steps 30 and 31, the Advertising packets are transmitted and received, and the SCAN Request packets are transmitted and received.

Next, in the step 35 (S35), the communication control unit 153 of the radio communication device 10 performs control to transmit the SCAN Response packets to the radio communication device 20. However, unlike the step 32, the communication control unit 153 performs control to transmit the SCAN Response packets not including the notification for limiting the purpose of the communication to the communication for the updating. Thus, the SCAN Response packets are transmitted, and the radio communication device 20 receives the SCAN Response packets.

Then, when the radio communication device 20 receives the SCAN Response packets in the step 35, the communication control unit 251 of the radio communication device 20 evaluates as to whether or not the radio communication device 10 has any problem as a correspondent. Although the radio communication device 20 does not hold the update information, holding the update information is not specified as the condition for establishing communication in the SCAN Response packets received in the step 35. Thus, the communication control unit 251 determines that the radio communication device 10 is appropriate as a correspondent.

Accordingly, in the step 36 (S36), the communication control unit 251 of the radio communication device 20 performs control to transmit the Connect Request packets to the radio communication device 10. Thus, the Connect Request packets are transmitted from the radio communication device 20, and the radio communication device 10 receives the Connect Request packets.

Then, in the step 37 (S37), the communication in the normal mode is established between the radio communication devices 10 and 20.

Figure 11:
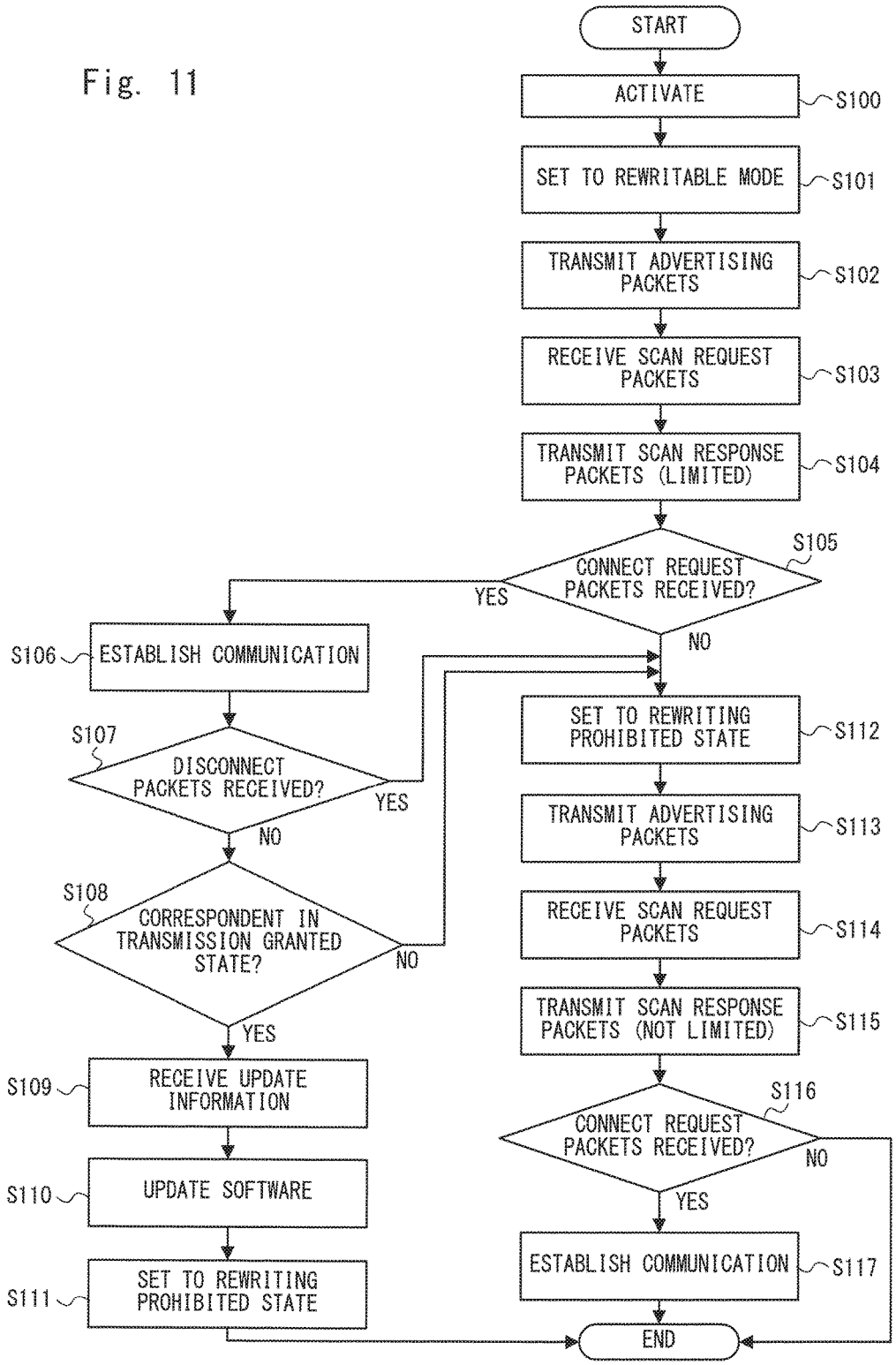
FIG. 11 is a flowchart showing an example of an operation of a radio communication device according to a first embodiment.

Next, details of the operation of the radio communication device 10 will be described by referring to the flowchart. FIG. 11 is a flowchart showing an example of the operation of the radio communication device 10.

In the step 100 (S100), the radio communication device 10 is powered on, and the radio communication device 10 is activated. The radio communication device 10 operates in the updating mode immediately after it is activated.

In the step 101 (S101), the rewrite switching unit 151 sets the radio communication device 10 to the rewritable state. That is, in the radio communication device 10, the software in the non-volatile memory 103 can be rewritten.

In the step 102 (S102), the transmission circuit 104 transmits the Advertising packets according to control by the communication control unit 153. Note that the step 102 corresponds to the step 20 in FIG. 9 and the step 30 in FIG. 10.

In the step 103 (S103), the reception circuit 105 receives the SCAN Request packets transmitted by the radio communication device 20. Note that the step 103 corresponds to the step 21 in FIG. 9 and the step 31 in FIG. 10.

In the step 104 (S104), the transmission circuit 104 transmits the SCAN Response packets including the notification for limiting the communication to the updating according to control by the communication control unit 153. Note that the step 104 corresponds to the step 22 in FIG. 9 and the step 32 in FIG. 10.

In the step 105 (S105), the communication control unit 153 evaluates as to whether or not the radio communication device 10 has received the Connect Request packets from the radio communication device 20. When the radio communication device 10 has received the Connect Request packets within a predetermined time (corresponding to the step 23 in FIG. 9), the process moves to the step 106. When the radio communication device 10 has not received the Connect Request packets within the predetermined time, the process moves to the step 112.

In the step 106 (S106), the communication control unit 153 establishes the communication according to BLE with the radio communication device 20. Note that the step 106 corresponds to the step 24 in FIG. 9.

In the step 107 (S107), the communication control unit 153 evaluates as to whether or not the radio communication device 10 has received the Disconnect packets from the radio communication device 20. When the radio communication device 10 has not received the Disconnect packets, the process moves to the step 108. When the radio communication device 10 has received the Disconnect packets, the process moves to the step 112.

In the step 108 (S108), the radio communication device 10 evaluates as to whether or not a state of the correspondent is a state capable of transmitting the update information. That is, the radio communication device 10 evaluates as to whether or not the state of the radio communication device 20 is in the transmission granted state. This evaluation can be performed by, for example, receiving a notification from the radio communication device 20 indicating as to whether the radio communication device 20 is in the transmission granted state or the transmission prohibited state. Alternatively, for example, the radio communication device 10 may determine that the radio communication device 20 is not in the state capable of transmitting the update information when the radio communication device 20 does not start transmitting the update information within a predetermined time. When the state of the correspondent is in the state capable of transmitting the update information, the process moves to the step 109. When the state of the correspondent is not in the state capable of transmitting the update information, the process moves to the step 112.

In the step 109 (S109), the reception circuit 105 receives the update information transmitted from the radio communication device 20.

Then, in the step 110 (S110), the update processing unit 152 applies the update information to the software to be updated that is stored in the non-volatile memory 103 in order to update the software.

After that, in the step 111 (S111), the radio communication device 10 ends the operation in the updating mode, and the rewrite switching unit 151 switches to the rewriting prohibited state. That is, the radio communication device 10 enters a state in which the rewriting of the software in the non-volatile memory 103 is prohibited.

On the other hand, when the process moves to the step 112 (S112), that is, when the communication establishment in the updating mode has failed (step 105: Yes), when the communication is disconnected (step 107: Yes), and when the radio communication device 20 is not in the transmission granted state (step 108: No), the radio communication device 10 ends the operation in the updating mode and starts the operation in the normal mode. Accordingly, in the step 112, the rewrite switching unit 151 is set to the rewriting prohibited state. From the step 112 onward, the communication control unit 153 attempts to establish the communication in the normal mode.

In the step 113 (S113), the transmission circuit 104 transmits the Advertising packets according to control by the communication control unit 153. Note that the step 113 corresponds to the step 33 in FIG. 10.

In the step 114 (S114), the reception circuit 105 receives the SCAN Request packets transmitted by the radio communication device 20. Note that the step 114 corresponds to the step 34 in FIG. 10.

In the step 115 (S115), the transmission circuit 104 transmits the SCAN Response packets not including the notification for limiting the communication to the updating according to control by the communication control unit 153. Note that the step 115 corresponds to the step 35 in FIG. 10.

In the step 116 (S116), the communication control unit 153 evaluates as to whether or not the radio communication device 10 has received the Connect Request packets from the radio communication device 20. When the radio communication device 10 has received the Connect Request packets within a predetermined time (corresponding to the step 36 in FIG. 10), the process moves to the step 117, while when the radio communication device 10 has received the Connect Request packets within the predetermined time, a series of processes is ended.

In the step 117 (S117), the communication control unit 153 establishes the communication according to BLE with the radio communication device 20. After that, the communication control unit 153 performs control to communicate except for receiving the update information. Note that the step 117 corresponds to the step 37 in FIG. 10

The operation example of the radio communication device 10 has been explained so far. With such a radio communication device 10, the radio communication system 1 operates, for example, as described below. When the radio communication device 20 does not hold the update information, the radio communication device 10 moves from the updating mode to the normal mode, and the radio communication system 1 operates as a heart rate meter system. On the other hand, when the radio communication device 20 downloads and holds latest software, the radio communication device 20 holds the update information. Thus, the communication is established in the establishment process of the communication in the updating mode. When the radio communication device 20 is set to the transmission granted state, the software is updated in the radio communication. On the other hand, when the radio communication device 20 is set to the transmission prohibited state, the updating is not executed, the radio communication device 10 moves to the normal mode, and the radio communication system 1 operates as a heart rate meter system.

Description of Advantages of First Embodiment

It is necessary to provide a switch for the software updating in the above radio communication device according to the comparative example. On the other hand, as the operation in the updating mode and the operation in the normal mode are automatically switched in the radio communication device 10 according to the first embodiment, such a switch is unnecessary, thereby reducing the cost. In the radio communication device according to the comparative example, it is necessary to operate the switch as indicated in the above step 902. On the other hand, in the radio communication device 10 according to the first embodiment, such an operation is unnecessary to update the software, thereby making it easy to update the software.

Moreover, as components for the updating including the switch can be eliminated, design flexibility of the radio communication device can be improved.

Second Embodiment

Next, a second embodiment will be described. In the first embodiment, the communication control unit 153 operates in the updating mode when the radio communication device 10 is activated. In this embodiment, when the communication is disconnected, the communication control unit 153 operates in the updating mode. That is, in this embodiment, the above-mentioned predetermined state indicates a state in which communication with another device is disconnected. When communication with another device is disconnected, the communication control unit 153 according to this embodiment operates in the updating mode. Then, the communication control unit 153 establishes communication when the communication control unit 153 receives the Connect Request packets in the communication establishment process in the updating mode. On the other hand, when the communication control unit 153 has not received the Connect Request packets in the communication establishment process in the updating mode, the communication control unit 153 operates in the normal mode and attempts to establish communication in the communication establishment process in the normal mode.

Figure 12:
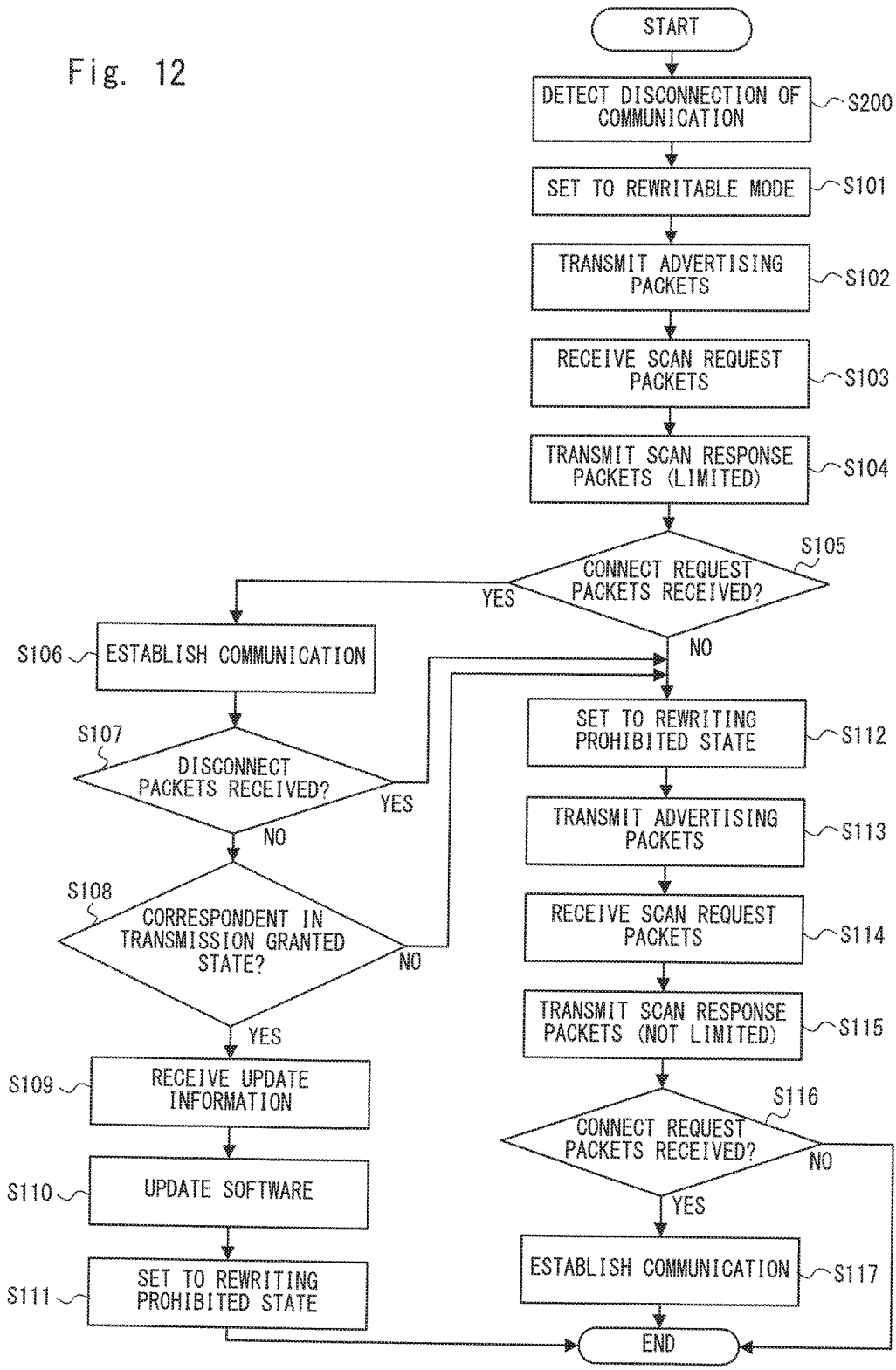
FIG. 12 is a flowchart showing an example of an operation of a radio communication device according to a second embodiment.

Description of Operation of Radio Communication Device 10 According to Second Embodiment Details of an operation of the radio communication device 10 according to this embodiment will be described by referring to the flowcharts. FIG. 12 is a flowchart showing an example of the operation of the radio communication device 10 according to the second embodiment. The flowchart shown in FIG. 12 is the same as the flowchart of the radio communication device 10 according to the first embodiment shown in FIG. 11 except that the step 100 in FIG. 11 is replaced by the step 200 in FIG. 12. Accordingly, the processes from the step 101 onward in FIG. 12 will not be described.

In the step 200 (S200), communication between the radio communication device 10 and another radio communication device is disconnected, and the communication control unit 153 detects the disconnection of the communication. The disconnection of the communication is not limited to the disconnection of the communication established in the normal mode but may include a disconnection of communication established in the updating mode. After the step 200, the process moves to the step 101. Thus, when the communication is disconnected, the process will proceed in a manner similar to that in the first embodiment.

Description of Advantages of Second Embodiment

Also in the radio communication device 10 according to this embodiment, the components for the updating including the switch can be eliminated, thereby reducing the cost. Further, the software can be easily updated. In particular, in the radio communication device 10 according to this embodiment, an execution timing of software update processing can be provided even while the radio communication device 10 is activated. Moreover, in the radio communication device 10 according to this embodiment, when the user wants to execute the update processing on the radio communication device 10, the user have only to disconnect the communication of the radio communication device 10. Accordingly, while the radio communication device 10 is activated, the user can easily execute the update processing of the radio communication device 10 at an arbitrary timing.

Although in this embodiment, it has been described that the communication control unit 153 operates in the updating mode when the communication is disconnected, the communication control unit 153 may operate in the updating mode also when the radio communication device 10 is activated.

Third Embodiment

Next, a radio communication device 10 according to a third embodiment will be described. The radio communication device 10 according to the third embodiment differs from the radio communication devices 10 of other embodiments in the point that when received strength of signals from another device is less than a predetermined threshold, the communication control unit 153 operates in the normal mode.

Further, the communication control unit 153 of this embodiment adjusts transmission/reception power according to the received strength of the signals from a correspondent. To be more specific, the lower the received strength of the signals from the other device, which is the correspondent, the greater the power used in the communication that is controlled by the communication control unit 153.

By the way, in general, as traffic increases more in the communication for the software updating than it does in the normal communication, the power consumption also increases in the communication for the software updating. Therefore, when the update processing is performed in the environment in which a communication environment is unfavorable, for example, when the radio communication devices 10 and 20 are distant from each other, the power consumption of the radio communication device 10 will be further increased. In this embodiment, in view of such circumstances, when the received strength is less than the threshold, the update processing is avoided, and an increase in the power consumption is prevented.

Figure 13:
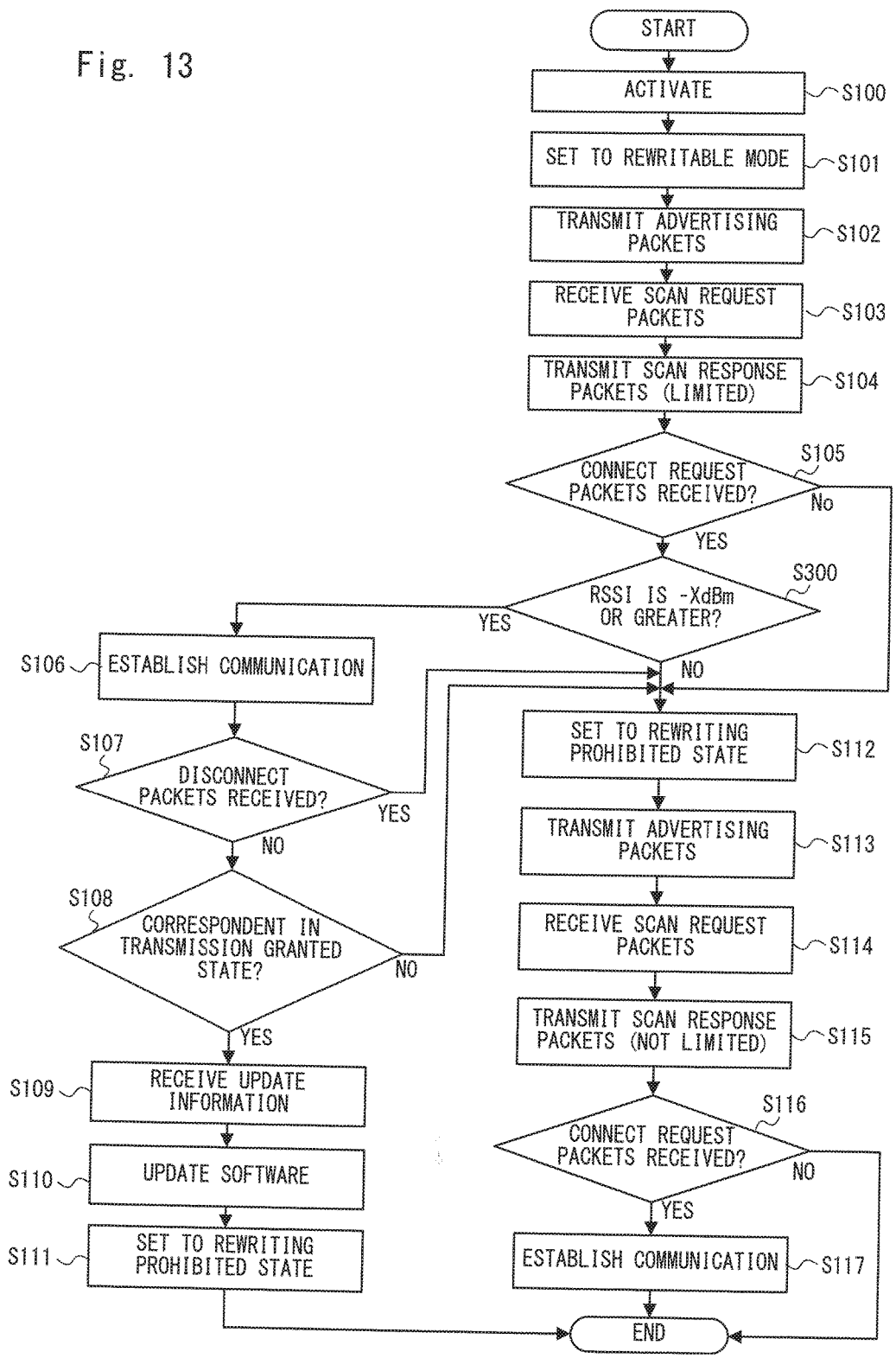
FIG. 13 is a flowchart showing an example of an operation of a radio communication device according to a third embodiment.

Description of Operation of Radio Communication Device 10 According to Third Embodiment Details of an operation of the radio communication device 10 according to this embodiment will be described by referring to the flowcharts. FIG. 13 is a flowchart showing an example of the operation of the radio communication device 10 according to the third embodiment. The flowchart shown in FIG. 13 differs from the flowchart of the radio communication device 10 according to the first embodiment shown in FIG. 11 in the point that the flowchart shown in FIG. 13 further includes the step 300. Thus, the difference between the flowcharts shown in FIGS. 13 and 11 will be focused below.

When the radio communication device 10 is activated, the rewrite switching unit 151 sets the radio communication device 10 to the rewritable state, and the communication unit 153 operates in the updating mode (steps 100 to 105). In the flowchart shown in FIG. 11, when the radio communication device 10 receives the Connect Request Packets in the evaluation in the step 105 of whether or not the Connect Request packets have been received, the process moves to the step 106. However, in such a case, in this embodiment, as shown in FIG. 13, the process moves to the step 300.

In the step 300 (S300), the communication control unit 153 evaluates as to whether or not received strength of signals from the radio communication device 20 is greater than or equal to a threshold. For example, the communication control unit 153 evaluates as to whether or not RSSI (Received Signal Strength Indication) is greater than or equal to a predetermined threshold (e.g., −XdBm). When the received strength of the signals from the radio communication device 20 is greater than or equal to the predetermined threshold, the process moves to the step 106, and communication is established. On the other hand, when the received strength of the signals from the radio communication device 20 is less than the threshold, the process moves to the step 112, and the radio communication device 10 starts the operation in the normal mode. As processing from the step 106 onward and processing from the step 112 onward are the same as the processing shown in the flowchart shown in FIG. 11, description thereof will be omitted.

As described above, in the radio communication device 10 according to the third embodiment, when the received strength of the signals from the radio communication device 20 is greater than or equal to the predetermined threshold, communication is established in the updating mode, and the update processing is executed in the updating mode. On the other hand, when the received strength of the signals from the radio communication device 20 is less than the predetermined threshold, the radio communication device 10 ends the operation in the updating mode and starts the operation in the normal mode.

Description of Advantages of Third Embodiment

Also in the radio communication device 10 according to this embodiment, the components for the updating including the switch can be eliminated, thereby reducing the cost. Further, the software can be easily updated. In particular, with the radio communication device 10 according to this embodiment, as the updating is executed only when the received strength is greater than or equal to the predetermined threshold, the update processing will not be executed in the environment in which great transmission/reception power is used because of low received strength, thereby preventing an increase in the power consumption.

Note that it is obvious that this embodiment can be combined with other embodiments as appropriate.

Fourth Embodiment

Next, a radio communication device 10 according to a fourth embodiment will be described. The radio communication device 10 according to the fourth embodiment differs from the radio communication devices 10 according to other embodiments in the point that the communication control unit 153 of the radio communication device 10 according to the fourth embodiment operates in the normal mode when software has been updated while the radio communication device 10 is activated last time.

Figure 14:
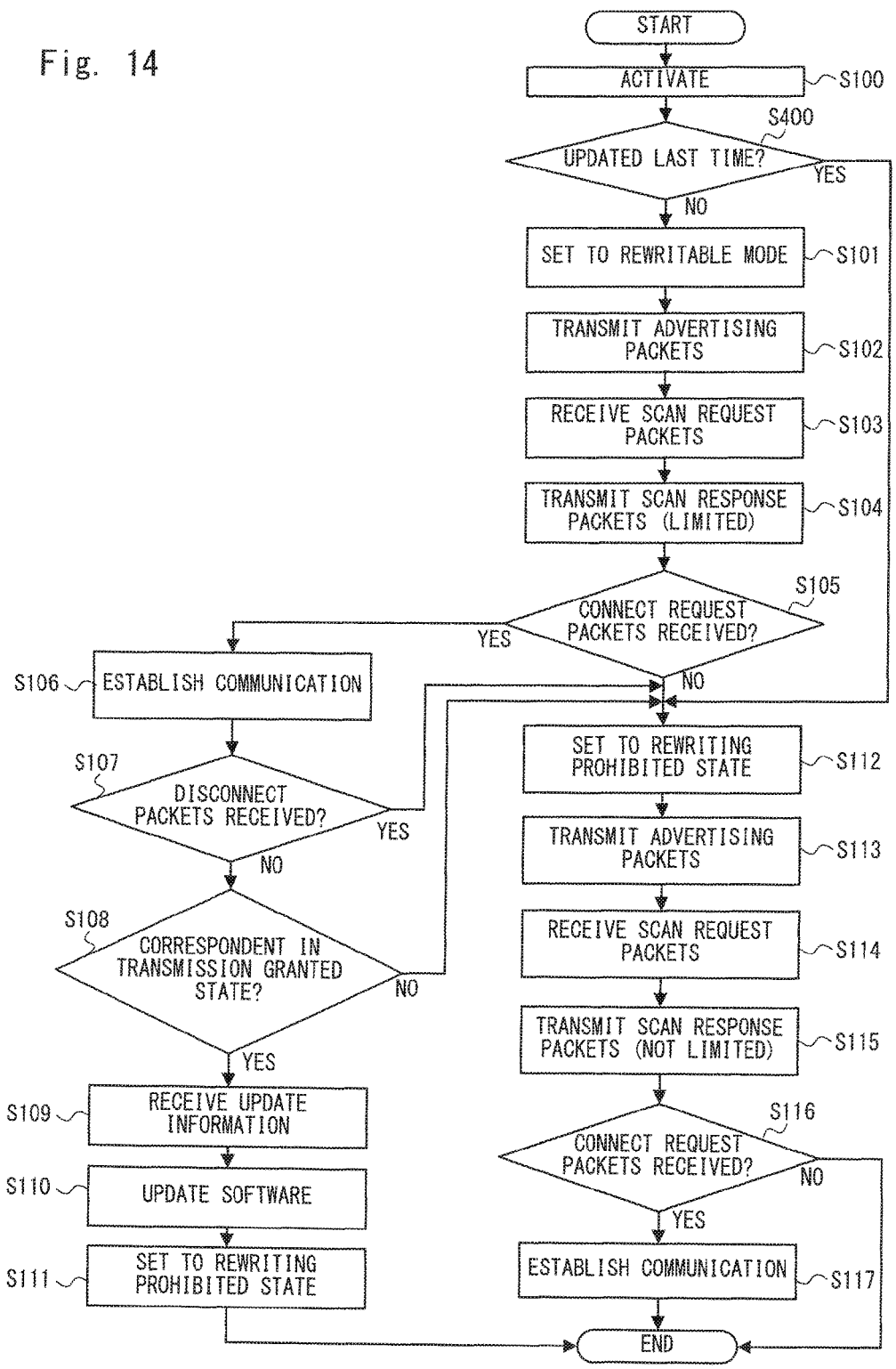
FIG. 14 is a flowchart showing an example of an operation of a radio communication device according to a fourth embodiment.

Description of Operation of Radio Communication Device 10 According to Fourth Embodiment Details of the operation of the radio communication device 10 according to this embodiment will be described by referring to the flowcharts. FIG. 14 is a flowchart showing an example of the operation of the radio communication device 10 according to the fourth embodiment. The flowchart shown in FIG. 14 differs from the flowchart of the radio communication device 10 according to the first embodiment shown in FIG. 11 in the point that the flowchart shown in FIG. 14 further includes the step 400. Thus, the difference between the flowcharts shown in FIGS. 14 and 11 will be focused below.

In this embodiment, when the radio communication device 10 is activated in the step 100, the process moves to the step 400. In the step 400 (S400), the communication control unit 153 evaluates as to whether or not the software has been updated while the radio communication device 10 is activated last time. The evaluation of whether or not the software has been updated while the radio communication device 10 is activated last time can be performed by various methods.

For example, the communication control unit 153 may use a boot swap function, which is a function to safely rewrite the non-volatile memory 103. The boot swap function swaps two boot clusters, which are physical memory regions. For example, the update processing unit 152 writes updated software in a boot cluster that is not a boot cluster storing the software before update from among the two boot clusters. After the update processing, the update processing unit 152 specifies the boot cluster in which the updated software has been written as a boot cluster to be accessed when the radio communication device 10 is activated next time. By doing so, the software before update can be backed up in either of the boot clusters, and there will be no problem in case of instantaneous power cut-off and the like because of the software backed up.

The communication control unit 153 evaluates as to whether or not the software has been updated while the radio communication device 10 is activated last time according to whether or not the boot cluster accessed when the radio communication device 10 is activated in the step 100 differs from the boot cluster when the radio communication device 10 is activated last time.

In the step 400, when it is evaluated that the software has not been updated while the radio communication device 10 is activated last time, that is, when it is evaluated, for example, that the boot cluster accessed when the radio communication device 10 is activated is the same as the boot cluster when the radio communication device 10 is activated last time, the process moves to the step 101. On the other hand, in the step 400, when it is evaluated that the software has been updated while the radio communication device 10 is activated last time, that is, when it is evaluated, for example, that the boot cluster accessed when the radio communication device 10 is activated differs from the boot cluster accessed when the radio communication device 10 is activated last time, the process moves to the step 112. Accordingly, when the software is updated while the radio communication device 10 is activated last time, the radio communication device 10 does not operate in the updating mode and operates in the normal mode after it is activated. As the processes from the step 101 onward are the same as those in the flowchart shown in FIG. 11, descriptions of those processes will be omitted.

Description of Advantages of Fourth Embodiment

Also in the radio communication device 10 according to this embodiment, the components for the updating including the switch can be eliminated, thereby reducing the cost. Further, the software can be easily updated. In particular, it is possible to prevent the radio communication device 10 according to this embodiment from unnecessarily operating in the updating mode. This contributes to reduction in the power consumption in this embodiment.

Note that it is obvious that this embodiment can be combined with other embodiments as appropriate.

Although the present invention carried out by the inventor has been described in detail, the present invention is not limited to the above embodiments, and it is obvious that various modifications can be made without departing from the scope of the invention. For example, the radio communication device 10 may not execute processing as a heart rate meter and may be a radio communication device that executes any processing using communication according to BLE. Further, in the above radio communication system 1, the radio communication device 20 does not necessarily provide the functions as a heart rate meter system and may be a radio communication device that merely provides the update information.

The whole or part of the embodiments disclosed above can be described as, but not limited to, the following supplementary notes.

(Supplementary Note 1)

A non-transitory computer readable medium storing a program that causes a computer of a radio communication device compliant with a Bluetooth (registered trademark) Low Energy standard to execute:

a first transmission step for transmitting advertising packets to another device;

a first reception step for receiving scan request packets from the other device in response to the advertising packets;

a second transmission step for transmitting first scan response packets in response to the scan request packets, the first scan response packets indicating that a condition for establishing communication is to include update information;

an updating step, when connect request packets in response to the first scan response packets are received, for establishing the communication with the other device, receiving the update information, and updating software of the radio communication device; and a communication step, when the connect request packets in response to the first scan response packets are not received, for transmitting the advertising packets to the other device, receiving the scan request packets in response to the advertising packets, transmitting second scan response packets not indicating that the condition for establishing the communication is to include the update information in response to the scan request packets, and when the connect request packets in response to the second scan response packets are received, establishing the communication with the other device, and performing communication other than reception of the update information.

(Supplementary Note 2)

A non-transitory computer readable medium storing the program according to Supplementary note 1, wherein in the updating step, the radio communication device is set to a rewritable state in which the software can be rewritten, and in the communication step, the radio communication device is set to a rewriting prohibited state in which the software is prohibited from being rewritten.

(Supplementary Note 3)

A non-transitory computer readable medium storing the program according to Supplementary note 1, wherein the first transmission step is performed when the radio communication device is activated.

(Supplementary Note 4)

A non-transitory computer readable medium storing the program according to Supplementary note 1, wherein the first transmission step is performed when the communication is disconnected.

(Supplementary Note 5)

A non-transitory computer readable medium storing the program according to Supplementary note 1, wherein in the updating step, when the connect request packets in response to the first scan response packets are received and received strength of signals from the other device is greater than or equal to a threshold, the update information is received, and the software in the radio communication device is updated.

(Supplementary Note 6)

A non-transitory computer readable medium storing the program according to Supplementary note 1, wherein when the software has not been updated while the radio communication device is activated last time, the first transmission step is performed when the radio communication device is activated.

(Supplementary Note 7)

A non-transitory computer readable medium storing the program according to Supplementary note 6, the program further causes the computer to execute an evaluation step for evaluating as to whether or not a memory region accessed when the radio communication device is activated is the same as the memory region when the radio communication device is activated last time, wherein in the updating step, between a first memory region and a second memory region, the updated software is written in one of the first and second memory regions that does not store the software before the updating, and the one of the first and second memory regions in which the updated software has been written is specified as a memory region to be accessed when the radio communication device is activated next time, and the first transmission step is performed when it is determined in the evaluation step that the memory region accessed when the radio communication device is activated is the same as the memory region when the radio communication device is activated last time.

The first to fourth embodiments can be combined as desirable by one of ordinary skill in the art.

While the invention has been described in terms of several embodiments, those skilled in the art will recognize that the invention can be practiced with various modifications within the spirit and scope of the appended claims and the invention is not limited to the examples described above.

Further, the scope of the claims is not limited by the embodiments described above.

Furthermore, it is noted that, Applicant's intent is to encompass equivalents of all claim elements, even if amended later during prosecution.

What is claimed is:

1. A radio communication device comprising:

a transmission unit;

a reception unit;

a communication control unit that uses the transmission unit and the reception unit to perform control on communication compliant with a Bluetooth (registered trademark) Low Energy standard to be executed in a first mode or a second mode;

a storage unit that stores software;

an update processing unit that updates the software;

a rewrite switching unit that switches to a rewritable state when the communication control unit operates in the first mode and to a rewriting prohibited state when the communication control unit operates in the second mode, the rewritable state being a state in which rewriting in the storage unit is granted, and the rewriting prohibited state being a state in which the rewriting is prohibited, wherein the first mode is a mode for receiving update information and updating the software, and in the first mode, the communication control unit transmits a notification for limiting the communication to the updating in an establishment process of the communication to another device, the second mode is a mode for performing processing other than the updating of the software, and in the second mode, the communication control unit does not transmit the notification for limiting the communication to the updating in the establishment process of the communication to the other device, when a state of the radio communication device corresponds to a predetermined state, the communication control unit operates in the first mode, while when the radio communication device does not receive connect request packets from the other device, the communication control unit operates in the second mode, and the update processing unit executes the updating when the communication is established in the first mode.

2. The radio communication device according to claim 1, wherein in the first mode, the communication control unit transmits first scan response packets indicating that a condition for establishing the communication is to include the update information in response to scan request packets from the other device, and in the second mode, the communication control unit transmits second scan response packets not indicating that the condition for establishing the communication is to include the update information in response to the scan request packets from the other device.

3. The radio communication device according to claim 1, wherein the predetermined state is a state when the radio communication device is activated, and when the radio communication device is activated, the communication control unit operates in the first mode, while when the radio communication device does not receive the connect request packets from the other device, the communication control unit operates in the second mode.

4. The radio communication device according to claim 1, wherein the predetermined state is a state in which the communication is disconnected, and when the communication is disconnected, the communication control unit operates in the first mode, while when the radio communication device does not receive the connect request packets from the other device, the radio communication devices operates in the second mode.

5. The radio communication device according to claim 1, wherein when received strength of signals from the other device is less than a predetermined threshold, the communication control unit operates in the second mode.

6. The radio communication device according to claim 1, wherein when the software has been updated while the radio communication device is activated last time, the communication control unit operates in the second mode.

7. The radio communication device according to claim 6, wherein between a first memory region and a second memory region in the storage unit, the update processing unit writes the updated software in one of the first and second memory regions that does not store the software before the updating and specifies the one of the first and second memory regions in which the updated software has been written as a memory region to be accessed when the radio communication device is activated next time, and when the memory region accessed when the radio communication device is activated differs from the memory region when the radio communication device is activated last time, the communication control unit determines that the software has been updated while the radio communication device is activated last time.

8. A method of controlling a radio communication device compliant with a Bluetooth (registered trademark) Low Energy standard, the method comprising:

a first transmission step for transmitting advertising packets to another device;

a first reception step for receiving scan request packets from the other device in response to the advertising packets;

a second transmission step for transmitting first scan response packets in response to the scan request packets, the first scan response packets indicating that a condition for establishing communication is to include update information;

an updating step, when connect request packets in response to the first scan response packets are received, for establishing the communication with the other device, receiving the update information, and updating software of the radio communication device; and a communication step, when the connect request packets in response to the first scan response packets are not received, for transmitting the advertising packets to the other device, receiving the scan request packets in response to the advertising packets, transmitting second scan response packets not indicating that the condition for establishing the communication is to include the update information in response to the scan request packets, and when the connect request packets in response to the second scan response packets are received, establishing the communication with the other device, and performing communication other than reception of the update information.

9. The method according to claim 8, wherein in the updating step, the radio communication device is set to a rewritable state in which the software can be rewritten, and in the communication step, the radio communication device is set to a rewriting prohibited state in which the software is prohibited from being rewritten.

10. The method according to claim 8, wherein the first transmission step is performed when the radio communication device is activated.

11. The method according to claim 8, wherein the first transmission step is performed when the communication is disconnected.

12. The method according to claim 8, wherein in the updating step, when the connect request packets in response to the first scan response packets are received and received strength of signals from the other device is greater than or equal to a threshold, the update information is received, and the software in the radio communication device is updated.

13. The method according to claim 8, wherein when the software has not been updated while the radio communication device is activated last time, the first transmission step is performed when the radio communication device is activated.

14. The method according to claim 13, further comprising an evaluation step for evaluating as to whether or not a memory region accessed when the radio communication device is activated is the same as the memory region when the radio communication device is activated last time, wherein in the updating step, between a first memory region and a second memory region, the updated software is written in one of the first and second memory regions that does not store the software before the updating, and the one of the first and second memory regions in which the updated software has been written is specified as a memory region to be accessed when the radio communication device is activated next time, and the first transmission step is performed when it is determined in the evaluation step that the memory region accessed when the radio communication device is activated is the same as the memory region when the radio communication device is activated last time.

15. A radio communication system comprising:
a first radio communication device; and
a second radio communication device, wherein
the first radio communication device comprises:
   a first transmission unit;
   a first reception unit;
   a first communication control unit that uses the first transmission unit and the first reception unit to perform control on communication compliant with a Bluetooth (registered trademark) Low Energy standard to be executed in a first mode or a second mode;
   a first storage unit that stores software;
   an update processing unit that updates the software;
   a rewrite switching unit that switches to a rewritable state when the first communication control unit operates in the first mode and to a rewriting prohibited state when the first communication control unit operates in the second mode, the rewritable state being a state in which rewriting in the first storage unit is granted, and the rewriting prohibited state being a state in which the rewriting is prohibited, wherein
the first mode is a mode for receiving update information and updating the software, and in the first mode, the first communication control unit transmits first scan response packets notifying that a condition for establishing the communication is to include the update information in response to scan response packets from the second radio communication device in an establishment process of the communication, the second mode is a mode for performing processing other than the updating of the software, and in the second mode, the first communication control unit transmits second scan response packets not indicating that the condition for establishing the communication is to include the update information in response to the scan response packets from the second radio communication device in the establishment process of the communication, when a state of the first radio communication device corresponds to a predetermined state, the first communication control unit operates in the first mode, while when the first radio communication device does not receive connect request packets from the second radio communication device, the first communication control unit operates in the second mode, and the update processing unit executes the updating when the communication is established in the first mode, and the second radio communication device comprises:
   a second transmission unit;
   a second reception unit;
   a second storage unit; and
   a second communication control unit that uses the second transmission unit and the second reception unit to perform control on communication compliant with the Bluetooth (registered trademark) Low Energy standard, wherein when the second storage unit holds the update information, the second communication control unit transmits the connect request packets in response to the first scan response packets.

16. The radio communication system according to claim 15, wherein the second radio communication device further includes an update execution control unit that controls as to whether or not to transmit the update information.

* * * * *